(12) United States Patent
Tsujii et al.

(10) Patent No.: US 8,787,527 B2
(45) Date of Patent: Jul. 22, 2014

(54) MAMMOGRAPHY APPARATUS

(75) Inventors: Osamu Tsujii, Kawasaki (JP);
Masakazu Morishita, Hiratsuka (JP);
Masahiko Okunuki, Akiruno (JP);
Satoshi Shimizu, Great Neck, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/114,144

(22) Filed: May 24, 2011

(65) Prior Publication Data

US 2011/0222652 A1  Sep. 15, 2011

Related U.S. Application Data

(63) Continuation of application No. 12/576,368, filed on Oct. 9, 2009, now Pat. No. 7,970,100.

(30) Foreign Application Priority Data

Nov. 6, 2008  (JP) ................................. 2008-285707

(51) Int. Cl.
*A61B 6/04* (2006.01)

(52) U.S. Cl.
USPC .......................................... 378/98.8; 378/37

(58) Field of Classification Search
USPC .................................................. 378/37, 98.8
See application file for complete search history.

(56) References Cited

U.S. PATENT DOCUMENTS

| | | | |
|---|---|---|---|
| 5,787,887 A | 8/1998 | Klingenbeck-Regn | 600/407 |
| 5,864,146 A | 1/1999 | Karellas | 250/581 |
| 5,998,794 A * | 12/1999 | Spivey et al. | 250/370.09 |
| 7,050,537 B2 | 5/2006 | Tsujii | 378/95 |
| 7,315,606 B2 | 1/2008 | Tsujii | 378/20 |
| 7,543,988 B2 | 6/2009 | Ramsauer | 378/206 |
| 7,564,998 B2 | 7/2009 | Tsujii | 382/128 |
| 7,742,561 B2 | 6/2010 | Ueki | 378/63 |
| 8,115,177 B2 | 2/2012 | Takeda et al. | 250/370.11 |

(Continued)

FOREIGN PATENT DOCUMENTS

| | | |
|---|---|---|
| DE | 103 32 301 A1 | 2/2005 |
| JP | 8-238233 | 9/1996 |

(Continued)

OTHER PUBLICATIONS

S. Fantini et al., "Using Near-Infrared Light to Detect Breast Cancer", *Optics & Photonics News*, Nov. 2003.

(Continued)

*Primary Examiner* — Hoon Song
(74) *Attorney, Agent, or Firm* — Fitzpatrick, Cella, Harper & Scinto

(57) ABSTRACT

A mammography apparatus includes a detector that detects X-rays transmitted through a breast, and an optically transparent or semitransparent pressing panel for pressing the breast. The apparatus further includes a near infrared ray source that provided between the X-ray source and the pressing panel and arranged in a two-dimensional shape in alignment with the pressing panel, and that is movable between a first position in close contact with the pressing panel and a second position outside an X-ray image capture region. Near infrared image capture is carried out using the near infrared ray source by causing the near infrared ray source to be in the first position, and the near infrared ray source is caused to retract to the second position when carrying out X-ray image capture using the X-ray source.

20 Claims, 7 Drawing Sheets

(56) References Cited

U.S. PATENT DOCUMENTS

| | | | |
|---|---|---|---|
| 2005/0111617 A1* | 5/2005 | Shoji | 378/37 |
| 2005/0226375 A1 | 10/2005 | Eberhard et al. | 378/62 |
| 2006/0019409 A1* | 1/2006 | Nelson et al. | 436/524 |
| 2006/0106293 A1 | 5/2006 | Fantini | 600/723 |
| 2007/0127625 A1* | 6/2007 | Hornig | 378/167 |
| 2008/0103740 A1 | 5/2008 | Meizoso Latova et al. | 703/7 |
| 2008/0279330 A1* | 11/2008 | Ueki | 378/63 |
| 2009/0118614 A1 | 5/2009 | Sendai | 600/437 |
| 2009/0232270 A1 | 9/2009 | Okunuki et al. | 378/5 |
| 2009/0232272 A1 | 9/2009 | Tsujii et al. | 378/16 |

FOREIGN PATENT DOCUMENTS

| | | |
|---|---|---|
| JP | 9-505407 | 5/1997 |
| JP | 2003-260046 | 9/2003 |
| JP | 2005-013344 | 1/2005 |
| JP | 2005/185472 | 7/2005 |
| JP | 2005-204810 A | 8/2005 |
| JP | 2007-225598 A | 9/2007 |
| JP | 2008-161283 | 7/2008 |
| JP | 2008-220555 A | 9/2008 |
| WO | WO 2008/053052 A | 5/2008 |

OTHER PUBLICATIONS

European Search Report issued in counterpart European Application No. 09 17 5065 dated Feb. 5, 2010—10 pages.

Z. Quan et al., "Coregistered Tomographic X-Ray and Optical Breast Imaging:Initial Result", *Journal of Biomedical Optics*, vol. 10, No. 2, 024033 (Mar. 2005), XP002562131.

Office Action issued Feb. 18, 2013 in counterpart Japanese Patent Application No. 2008-285707, with translation.

A. da Silva et al., "Coupling X-Ray and Optical Tomography Systems for in vivo Examination of Small Animals", *Proceedings of the 29th Annual International Conference of the IEEE EMBS*, pp. 3335-3338 (Aug. 23, 2007).

Extended European Search Report issued Dec. 21, 2012, in counterpart European Patent Application 12187123.0.

Office Action issued on May 17, 2013 in counterpart Japanese Patent Application No. 2008-285707, with partial translation.

S. Fantini et al., "Instrumentation and Clinical Applications in Frequency-Domain Optical Mammography", *IEEE,/EMBS, Proceedings of the 19$^{th}$ International Conference*, Oct. 30-Nov. 2, 1997, pp. 2741-2744 (1997).

* cited by examiner

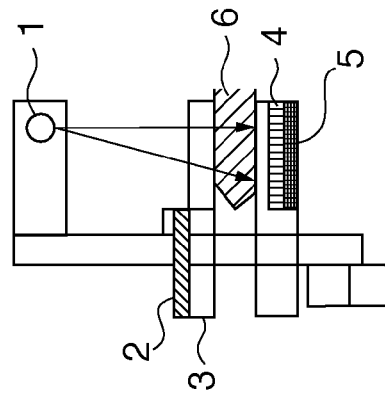
FIG. 1D WHEN OBTAINING AN X-RAY IMAGE
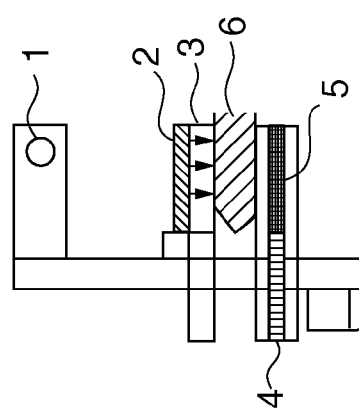
FIG. 1C WHEN OBTAINING A NEAR INFRARED IMAGE AND WHEN BREAST POSITIONING
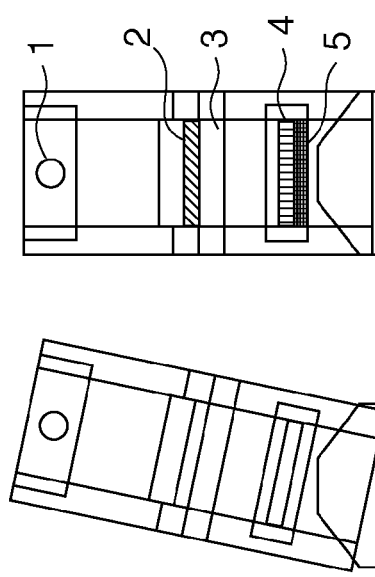
FIG. 1B FRONT VIEW (WHEN CC)
FIG. 1A FRONT VIEW (WHEN MLO)

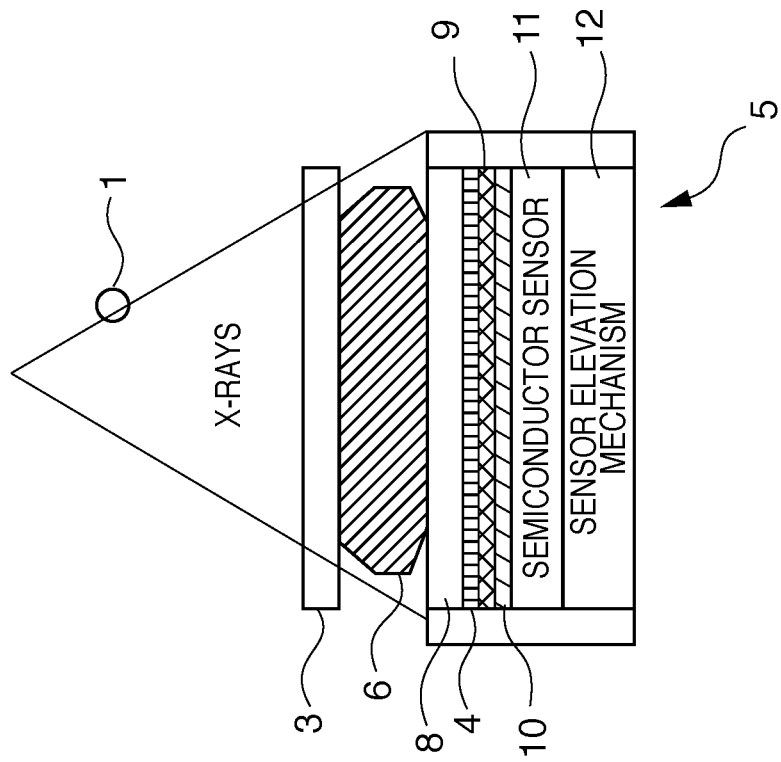
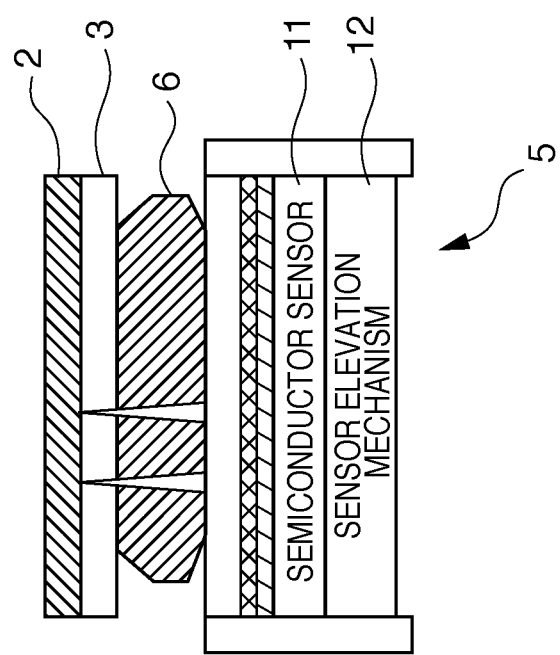

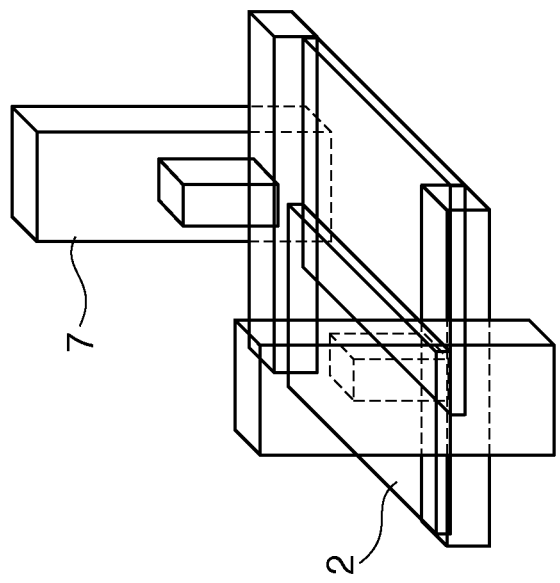
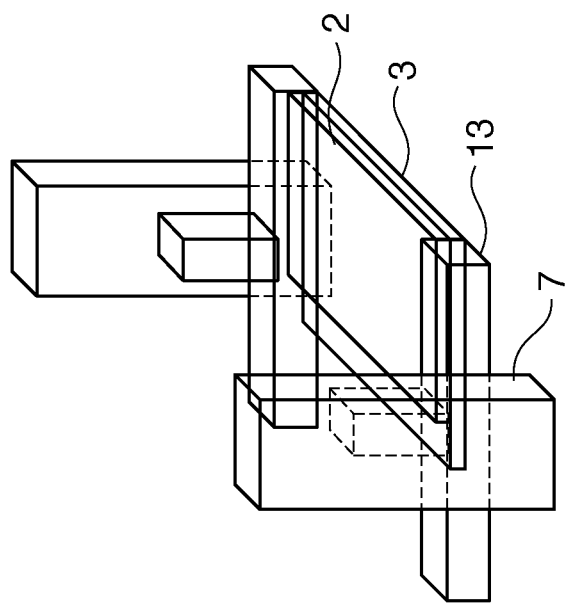
FIG. 4A
FIG. 4B

F I G. 5A    F I G. 5B
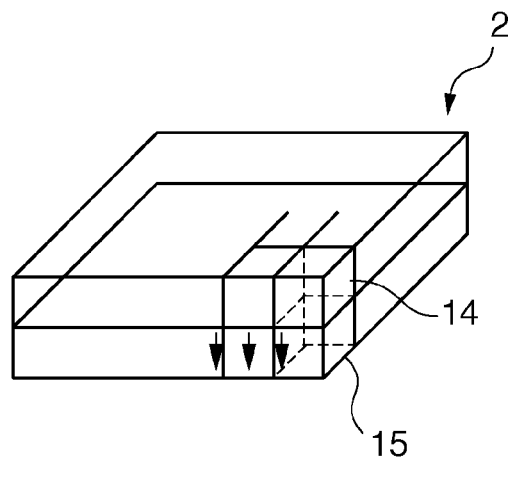
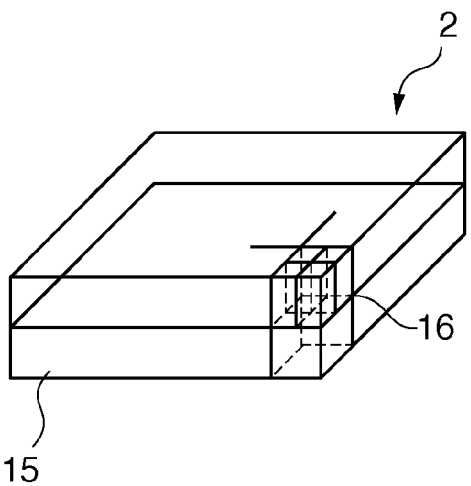
F I G. 6
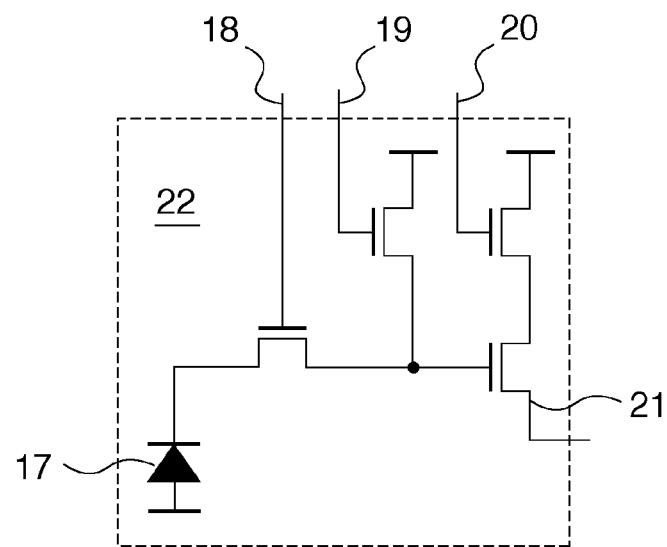

MAMMOGRAPHY APPARATUS

RELATED APPLICATIONS

This is a continuation of application Ser. No. 12/576,368, filed Oct. 9, 2009, claims benefit of that application under 35 U.S.C. §120, and claims benefit under 35 U.S.C. §119 of Japanese Patent Application No. 2008-285707, filed Nov. 6, 2008. The entire contents of each of the mentioned prior applications are incorporated herein by reference.

BACKGROUND OF THE INVENTION

1. Field of the Invention

The present invention relates to mammography apparatuses that obtain X-ray images of mammary specimens using X-ray imaging.

2. Description of the Related Art

Mammography apparatuses that obtain X-ray images of mammary specimens using X-ray imaging include mammography apparatuses that use semiconductor two-dimensional image detectors. These are configured mainly with an X-ray source, a pressing panel for pressing the breast, a two-dimensional X-ray image detector that holds the breast and images an intensity distribution of transmitted X-rays. Two-dimensional image detectors are produced by combining phosphor, which converts the X-rays to visible fluorescence, and a semiconductor two-dimensional image detector (see Japanese Patent Laid-Open No. 08-238233 for example).

Some mammography apparatuses use a grid to suppress scattered X-rays (see Japanese Patent Laid-Open No. 2005-013344 for example).

Furthermore, some apparatuses perform imaging with the X-ray image and an ultrasonic image of the breast under a same pressing condition. For example, infrared rays are used in a sensor that detects a position of an ultrasonic probe in regard to these apparatuses. The breast is pressed in a same manner for obtaining the X-ray image and for obtaining the ultrasonic image, and therefore as a result it is possible to combine the ultrasonic image and the X-ray image (see Japanese Patent Laid-Open No. 2003-260046 for example).

Furthermore, techniques have been proposed (see Japanese Patent Laid-Open No. 09-505407 for example) in which a breast image is captured by irradiating near infrared rays onto a breast through a breast compressing panel and collecting transmitted light using optic fibers.

Further still, techniques have been proposed (for example, see Sergio Fantini et al, "Using Near-Infrared Light To Detect Breast Cancer," Optics & Photonics News, November, 2003) in which a near infrared image of a breast is obtained by causing a plurality of amplitude-modulated near infrared rays to be incident on a single optic fiber then transmitting this onto the breast and performing homodyne detection on the transmitted near infrared rays.

In breast cancer diagnosis using mammography apparatuses, reproducibility of positioning between the imaging apparatus and the breast is sometimes required for cytology and histology in a case where a positive result is doubted or during postoperative observations over time.

However, conventional mammography apparatuses do not have a positioning function.

On the other hand, although there are cases where near infrared images are effective in discovering tumorous cancer, which is a weak point for X-ray images, there is a problem in that it has not been possible to achieve a correspondence between the positions of the morbid portion discovered in the near infrared image and the X-ray image.

SUMMARY OF THE INVENTION

In light of the foregoing problems, the present invention provides a mammography apparatus capable of reproducing breast positioning during breast X-ray imaging for example.

In one aspect of the present invention, a mammography apparatus for capturing an X-ray image of a breast, comprises an X-ray source, a detector having a placement surface on which a breast is placed on a side opposing the X-ray source and that detects X-rays transmitted through the breast, wherein the detector is capable of detecting near infrared rays as well as being capable of detecting X-rays, an optically transparent or semitransparent pressing panel for pressing the breast that is placed on the placement surface against the placement surface, a two-dimensional near infrared ray source that is provided between the X-ray source and the pressing panel and arranged in a two-dimensional shape in alignment with the pressing panel, and that is movable between a first position in close contact with the pressing panel and a second position outside an X-ray image capture region, and a controller that carries out near infrared image capture using the two-dimensional near infrared ray source by causing the two-dimensional near infrared ray source to be in the first position, and causes the two-dimensional near infrared ray source to retract to the second position when carrying out X-ray image capture using the X-ray source.

Further features of the present invention will become apparent from the following description of exemplary embodiments with reference to the attached drawings.

BRIEF DESCRIPTION OF THE DRAWINGS

FIGS. 1A to 1D are outlines of a mammography apparatus according to the present embodiment.

FIGS. 3A and 3B are diagrams showing a structure of a two-dimensional detector.

FIGS. 4A and 4B are diagrams showing advancement and retraction of a laser diode matrix.

FIGS. 5A and 5B are diagrams showing a structure of a laser diode matrix.

FIG. 6 is a diagram showing one pixel of a semiconductor sensor.

DESCRIPTION OF THE EMBODIMENTS

Figure 2:
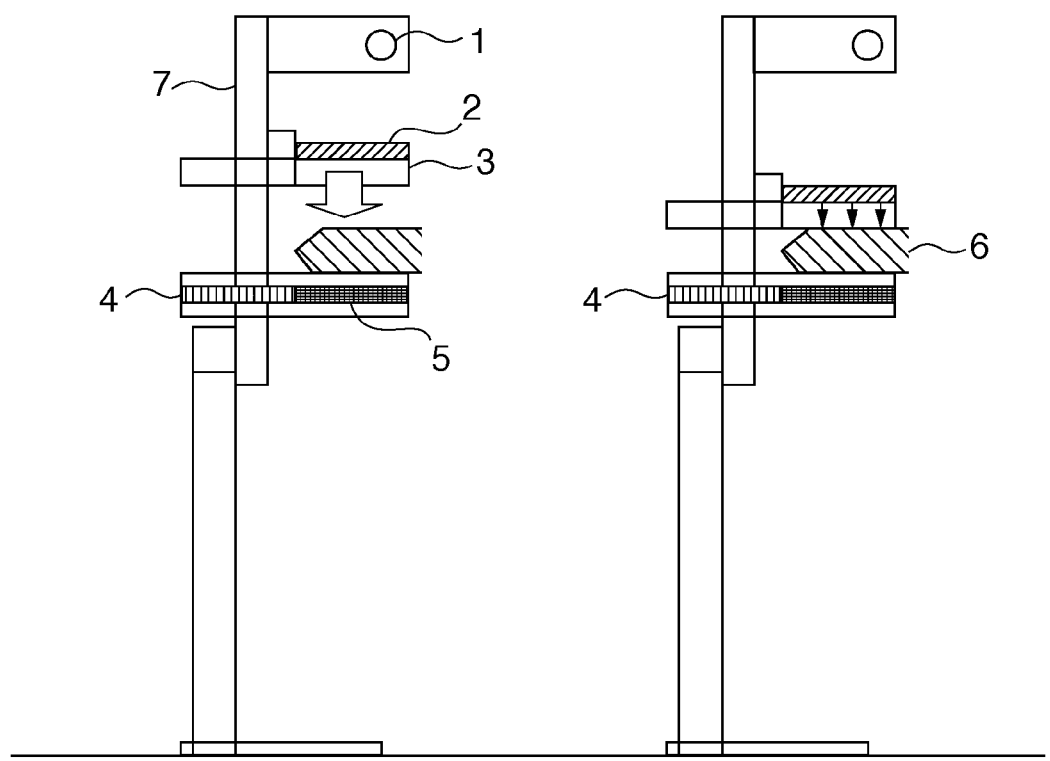
FIG. 2 is a diagram showing operation of a pressing panel when capturing an image for breast positioning.

Various exemplary embodiments, features, and aspects of the present invention will be described in detail below with reference to the drawings.

FIGS. 1A to 1D show outlines of a mammography apparatus according to the present embodiment.

FIG. 1B is a front view showing a state of the apparatus when capturing a CC (cranio-caudad) image of a breast 6, and is a diagram in which the mammography apparatus is viewed from an examinee (patient). Arranged in order from above are an X-ray source 1, a laser diode matrix 2, a pressing panel 3, an X-ray grid 4, and a two-dimensional detector 5. FIG. 1A is a front view showing a state of the apparatus when capturing an MLO (medio-lateral oblique) image of the breast 6. A difference from the front view (when CC) of FIG. 1B is that a capture section is tilted.

Here, the two-dimensional detector 5 is a detector having a placement surface on which the breast 6 is placed on a side opposing the X-ray source 1.

Description is given of a state of the apparatus at a time of obtaining an infrared image and a time of breast positioning shown in FIG. 1C. In this state, no X-rays are exposed from the X-ray source 1. The breast 6 of an examinee placed on the placement surface of the two-dimensional detector 5 is pressed by the pressing panel 3 against the placement surface. The laser diode matrix 2, which is a two-dimensional near infrared ray source arranged in a two-dimensional shape in alignment with the pressing panel 3, is provided above the pressing panel 3. The laser diode matrix 2 is configured to be movable between a first position in close contact with the pressing panel 3 and a second position outside an X-ray image capture region. A plurality of near infrared laser diodes are arranged in a matrix shape in the laser diode matrix 2. The pressing panel 3 is an optically transparent or semitransparent material through which near infrared rays are transmitted, and is a material through which X-rays are readily transmitted, for example an acrylic or the like is appropriate.

The near infrared rays emitted from the near infrared laser diodes are transmitted through the pressing panel 3 and proceed while undergoing attenuation and diffusion through the breast 6 to reach the two-dimensional detector 5. The X-ray grid 4 that does not transmit near infrared rays is retracted. The two-dimensional detector 5 includes a two-dimensional semiconductor detector having sensitivity to visible light and near infrared ray. That is, the two-dimensional detector is capable of detecting visible light and near infrared rays as well as being capable of detecting X-rays. A near infrared image of the breast 6 is calculated based on an intensity distribution of light incident on the two-dimensional detector 5. Here, the time of breast positioning is used because by displaying a near infrared image of the breast 6 in real time, an imaging technician becomes capable of reproducing a positioning state of the breast 6 based on vascular arrangement in the breast 6.

Description is given regarding differences between imaging for breast positioning and imaging of near infrared images. All of these images are formed using near infrared rays. However, at a time of imaging for breast positioning, increased speeds in image forming times are required for the imaging technician to respond to changes in the breast settings. In this regard, time is required in imaging a breast spectroscopic image using near infrared laser diodes of multiple wavelengths in the laser diode matrix 2.

Shortening the imaging times becomes possible by decimating rather than lighting all the laser diodes incorporated in the laser diode matrix 2, thereby sacrificing image resolution to give priority to real time capabilities.

Compared to imaging for breast positioning, imaging of near infrared images is high resolution, and although it is spectroscopic, the imaging times become longer.

Next, description is given of a state of the apparatus shown in FIG. 1D when capturing an X-ray image.

The X-ray image is captured after breast positioning is completed. When imaging for breast positioning and imaging of the near infrared image are completed, the laser diode matrix 2 retracts from the X-ray image capture region.

On the other hand, the retracted X-ray grid 4, which is retracted at a time of imaging for breast positioning, is inserted above the two-dimensional detector 5. When the retraction of the laser diode matrix 2 and the insertion of the X-ray grid 4 are confirmed, X-rays are exposed.

In this regard, there is a correlation between a transmission amount of near infrared rays when imaging a near infrared image and a transmission amount of X-rays. A positive correlation is known between breast thickness and mammary gland density and the amount of light that reaches the two-dimensional detector 5. Using this relationship, it is possible to determine an X-ray target, an X-ray filter, an X-ray tube current, and an imaging time when imaging an X-ray image. For example, in a case where the amount of light that reaches the detector is a specific value or less, it is conceivable to use rhodium as the X-ray target rather than molybdenum. Furthermore, it is possible to increase the X-ray tube current inversely proportional to the amount of light that reaches the detector. In a case where the X-ray tube current cannot be increased due to a limitation of the X-ray source, the imaging time is increased.

FIG. 2 indicates an operation of the pressing panel 3 when capturing an image for breast positioning and a timing of lighting the near infrared laser diodes. Although the position setting of the breast and the commencement of breast pressing are determined by the imaging technician while confirming the safety of the patient, the lighting of the laser diodes commences automatically when a predetermined pressing force or greater is applied to the pressing panel 3. When capture of the positioning image is completed, the lighting of the laser diodes stops.

Positioning images are displayed on a display device not shown in the diagrams. When the imaging technician judges that the positioning is appropriate, a transition is made to capturing a high resolution near infrared image. Images for judging the suitability of positioning can include displaying a difference image between a past image and a current image as well as being displayed in parallel to a previously captured image. A relative relationship between the images is important in forming a difference image. A correlation coefficient of the two images can be calculated as an indicator of the relative relationship. By performing image shifting based on the correlation coefficient in a direction in which the correlation coefficient becomes larger, better positioning can be achieved.

FIGS. 3A and 3B are diagrams showing a structure of the two-dimensional detector 5.

When capturing an image for positioning and a near infrared image shown in FIG. 3A, the laser diode matrix 2 is arranged in close contact to an upper surface of the pressing panel 3. Hereinafter, an image for positioning and a near infrared image are both indicated when referring to a near infrared image.

Near infrared rays that have been transmitted through the pressing panel 3 and the breast 6 are incident on the two-dimensional detector 5. The two-dimensional detector 5 has a protective panel 8, a wavelength filter 9, an X-ray phosphor 10, a semiconductor sensor 11, and a sensor elevation mechanism 12.

The protective panel 8 protects the semiconductor sensor 11 during breast pressing. The protective panel 8 is a material having little X-ray attenuation and through which near infrared rays are transmitted. For example, acrylic or reinforced glass can be used.

The wavelength filter 9 is a filter that transmits near infrared rays or rays of longer wavelengths than near infrared rays, and is a film through which visible light and far infrared rays are not transmitted.

The X-ray phosphor 10 transmits near infrared rays, and generates fluorescence with respect to incident X-rays. A CsI columnar crystal is appropriate as an example of the X-ray phosphor 10. Because it is columnar, diffusion of X-ray fluorescence and near infrared rays can be reduced.

A CMOS sensor for example can be used as the semiconductor sensor 11. Amorphous silicon sensors widely used in X-ray images cannot be used since they have no sensitivity to near infrared.

The sensor elevation mechanism 12 is a mechanism for adjusting the distance between the lower surface of the protective panel 8 and the upper surface of the wavelength filter 9. By bringing the lower surface of the protective panel 8 and the upper surface of the wavelength filter 9 close together, it is possible to reduce resolution deterioration in near infrared images.

When performing breast imaging, high resolution is demanded for the X-ray image, and for example a pixel pitch of 100 µm is necessary.

However, since X-ray images are still images, high speed image readout is not required. On the other hand, a required resolution of near infrared images is approximately 1 to 3 mm. High speed image readout is necessary for near infrared images.

Accordingly, with a pixel size of 100 µm, the structure of the semiconductor sensor 11 is a structure capable of reading clusters of 8×8 images, 16×16 images, or 32×32 pixels.

Furthermore, although X-ray images are formed at one time over the entire surface of the semiconductor sensor 11, near infrared images are limited to a region of approximately 10 mm×10 mm with respect to a single laser diode. Thus, when capturing a near infrared image, it is necessary to perform partial (local) high speed reading at the same time as cluster reading.

Furthermore, the semiconductor sensor 11 changes the image pickup region in response to the resolution that is set when capturing a near infrared image. A relative positional relationship between the laser diode matrix 2 and the two-dimensional detector 5 can be known in advance by calibration.

Next, description is given of a structure of FIG. 3B when capturing an X-ray image.

When capturing an X-ray image, the laser diode matrix 2 retracts and the X-ray grid 4 is inserted between the protective panel 8 and the wavelength filter 9. The X-ray grid 4 has an effect of reducing X-ray scattering. A gap between the protective panel 8 and the wavelength filter 9 is formed by downwardly shifting as a group the wavelength filter 9, the X-ray phosphor 10, and the semiconductor sensor 11 using the sensor elevation mechanism 12.

On the other hand, it is also possible to bring the wavelength filter 9 in close contact with the lower surface of the protective panel 8 and insert the X-ray grid 4 in a gap between the wavelength filter 9 and the X-ray phosphor 10. However, from a perspective of shielding the semiconductor sensor 11, the foregoing method of inserting the X-ray grid 4 between the protective panel 8 and the wavelength filter 9 is beneficial.

In this regard, a commonly known X-ray grid 4 is not a structure that transmits near infrared rays. The X-ray grid 4 is a structure in which wood or fiber or the like is sandwiched between lead foil.

However, it is possible to sandwich between the lead foil a fiber that transmits near infrared rays.

When an X-ray grid 4 such as this capable of transmitting near infrared rays is used, the operations of inserting and retracting the grid become unnecessary, and optical shielding of the two-dimensional detector 5 is easy.

FIGS. 4A and 4B show advancement and retraction of the laser diode matrix 2.

The pressing panel 3 is secured on a pressing panel support frame 13. The pressing panel support frame 13 is installed so as to be capable of vertical movement on a support upper frame 7 of the imaging apparatus.

As shown in FIG. 4A, when capturing a near infrared image, the laser diode matrix 2 slides on the pressing panel support frame 13 and advances over the pressing panel 3. After advancement, the laser diode matrix 2 is brought in close contact with the pressing panel 3 using a suction or a pressure clamping mechanism (not shown in diagrams).

As shown in FIG. 4B, when capturing an X-ray image, the laser diode matrix 2 slides on the pressing panel support frame 13 to retract after the close contact is released.

FIGS. 5A and 5B show a structure of the laser diode matrix 2. The laser diode matrix 2 is a two-layer structure.

First, description is given of an example in FIG. 5A.

In an upper portion, laser diodes 14 are arranged two-dimensionally, and in a lower portion, fibers are arranged two-dimensionally. The laser diodes 14 and the fibers are made to correspond one to one, and adhered, pressed, or bound together.

In the example of FIG. 5B, four near infrared laser diodes 16 of different frequencies correspond to a single fiber as a group. By using near infrared rays of multiple frequencies, spectroscopy of the breast 6 can be achieved.

In a case of achieving spectroscopy, four near infrared laser diodes 16 having different frequencies are made to correspond to a single fiber in the working example shown in FIG. 5B, but it is also possible to make a laser diode of each frequency corresponds to a single fiber.

FIG. 6 shows one pixel of the semiconductor sensor 11. Light incident on a photo diode 17 is converted to an electrical signal, a transfer switch signal 18 becomes ON, and then the signal is output via a preamplifier by undergoing line selection.

Figure 7:
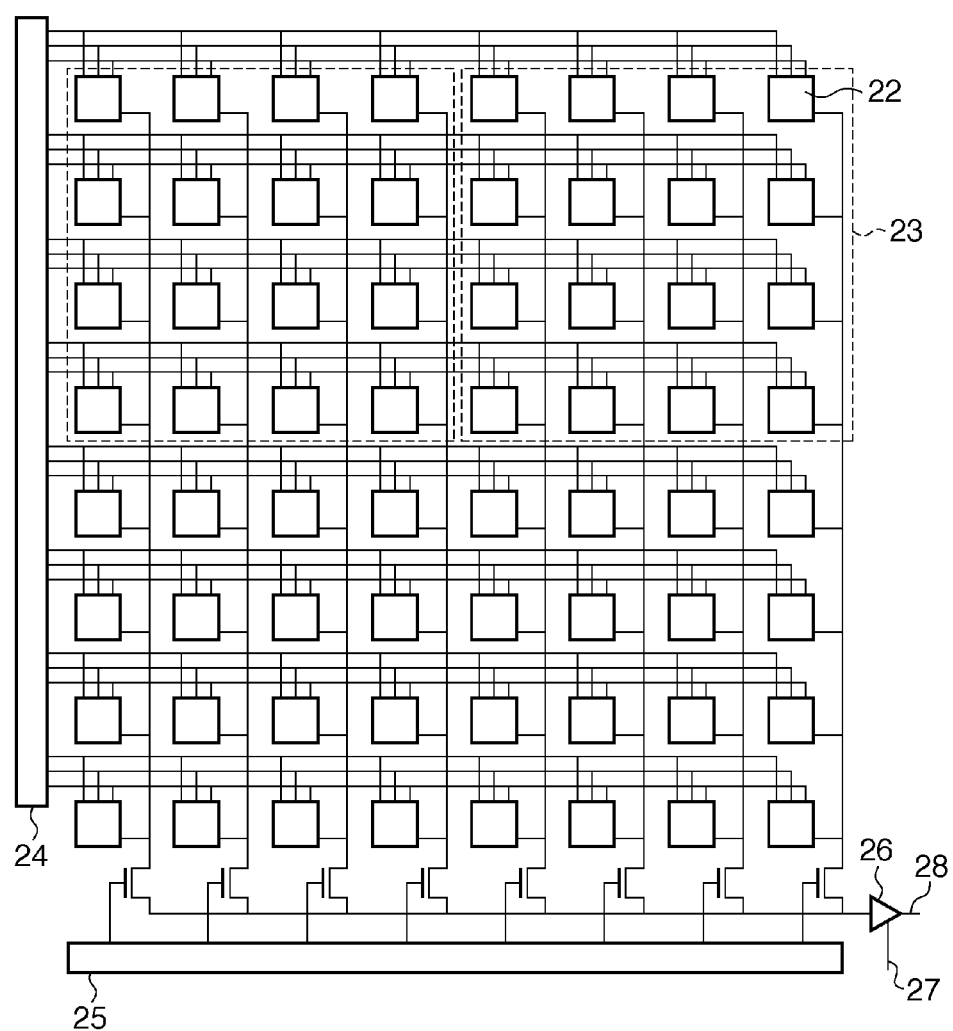
FIG. 7 is a diagram in which pixels of the semiconductor sensor are arranged two-dimensionally.

FIG. 7 is a diagram in which pixels of FIG. 6 are arranged two-dimensionally. Output of each pixel in an 8×8 array is selected by a vertical shift register 24 and a horizontal shift register 25. Output of a selected pixel is outputted via an amplifier 26. To capture an entire breast image, a two-dimensional detector 5 is necessary having an effective area of at least 20 cm×24 cm. This size can be achieved with a single semiconductor sensor 11 using amorphous silicon, but for a crystal semiconductor such as CMOS, this size is currently impossible. On the other hand, when capturing a near infrared image, high speed local readouts are necessary. Accordingly, in the present embodiment, sensors of approximately 256× 256 pixels are arranged in a tile shape to achieve an overall size of approximately 20 cm×24 cm.

Description is given regarding a function of the amplifier 26 of FIG. 7.

When reading out an X-ray image, pixels are selected one by one by the vertical shift register 24 and the horizontal shift register 25. A constant multiple setting is performed for a gain change signal 27, and therefore a signal of the selected signal is amplified by the constant multiple and output. When reading out the near infrared image, pixels of a range surrounded by the dashed line are selected and output at the same time. In the case of FIG. 7, 4×4 pixels are selected at the same time. An added signal of selected pixel signals is amplified by the amplifier 26. Gain change is performed using the gain change signal 27 during amplification. A signal of a frequency approximating a frequency of an intensity modulated signal of the laser diodes is used as the gain change signal 27.

Spectroscopic imaging methods using near infrared rays are described in detail in the above-mentioned Sergio Fantini et al, "Using Near-Infrared Light To Detect Breast Cancer,"

Optics & Photonics News, November, 2003. Here, simple description is given of a method in which near infrared rays of four wavelengths are used.

Laser diode lights of 690 nm, 750 nm, 788 nm, and 856 nm are used for the four wavelengths. The light of the four wavelengths undergoes amplitude modulation at 70.45 MHz, 70.20 MHz, 69.80 MHz, and 69.5 MHz respectively.

Amplitude modulated light is made incident on the breast 6 clustered into a single fiber as shown in the structure shown in FIG. 5B. Light that is transmitted through the breast 6 is incident on a single region of cluster reading pixels 23 shown in FIG. 7. Incident signals are amplified by the amplifier 26, and a 70 MHz signal is used in the gain change signal 27 when amplifying.

Signals of four wavelengths are separated from a gain change output signal 28 such that four near infrared images can be formed.

Spectroscopy is created by combining the four images using image processing. This system is referred to as frequency domain optical mammography, but the near infrared images used in the present invention are not limited to this system, and configurations according to the present invention can be used in other systems also.

Description is given regarding a case where differences occur from the frequency domain system disclosed in Sergio Fantini et al, "Using Near-Infrared Light To Detect Breast Cancer," Optics & Photonics News, November, 2003. When collecting near infrared rays, in the foregoing description, only a single location of cluster reading pixels 23 are read out with respect to emitted rays of the single laser diode (in the case of FIG. 5B, four laser diodes forming a single group).

However, when consideration is given to a case where diffusion information of the near infrared rays also includes information, it is conceivable to read out multiple cluster reading pixels 23.

For example, when reading out four cluster reading pixels 23, reading is performed serially (successively), and therefore phase differences occur in the gain change.

Accordingly, it is necessary to give consideration that there are phase differences between the four pixels when extracting beats using homodyne detection. Note however that the phase differences of the four cluster reading images are already known since these correspond to a read-in frequency of the semiconductor sensor.

Description is given regarding an image correction method. In conventional two-dimensional detectors 5 specialized for X-ray images, a thin aluminum sheet is used instead of the wavelength filter 9. In this case, there is no risk that visible light, near infrared rays, or infrared rays will be incident. However, depending on characteristics of the wavelength filter 9, there is a risk that small amounts of visible light, near infrared rays, or infrared rays will be incident on the semiconductor sensor 11 when near infrared rays are not being emitted from the laser diodes.

Furthermore, the structure is complicated compared to the conventional two-dimensional detector 5 specialized for X-ray images, and therefore there is also a risk that the above-mentioned light will be incident in minute amounts. These lights become offsets and reduce the contrast in images.

Consequently, before capturing the near infrared image of FIG. 3A and capturing the X-ray image, black images (dark images) are captured respectively and subtracted from the acquired images respectively. Furthermore, shading correction is possible by capturing a white image when capturing the near infrared image and when capturing the X-ray image respectively and dividing these by the acquired images. The white image is an image in a case where the laser diodes or X-rays are emitted while there is no subject.

Figure 8:
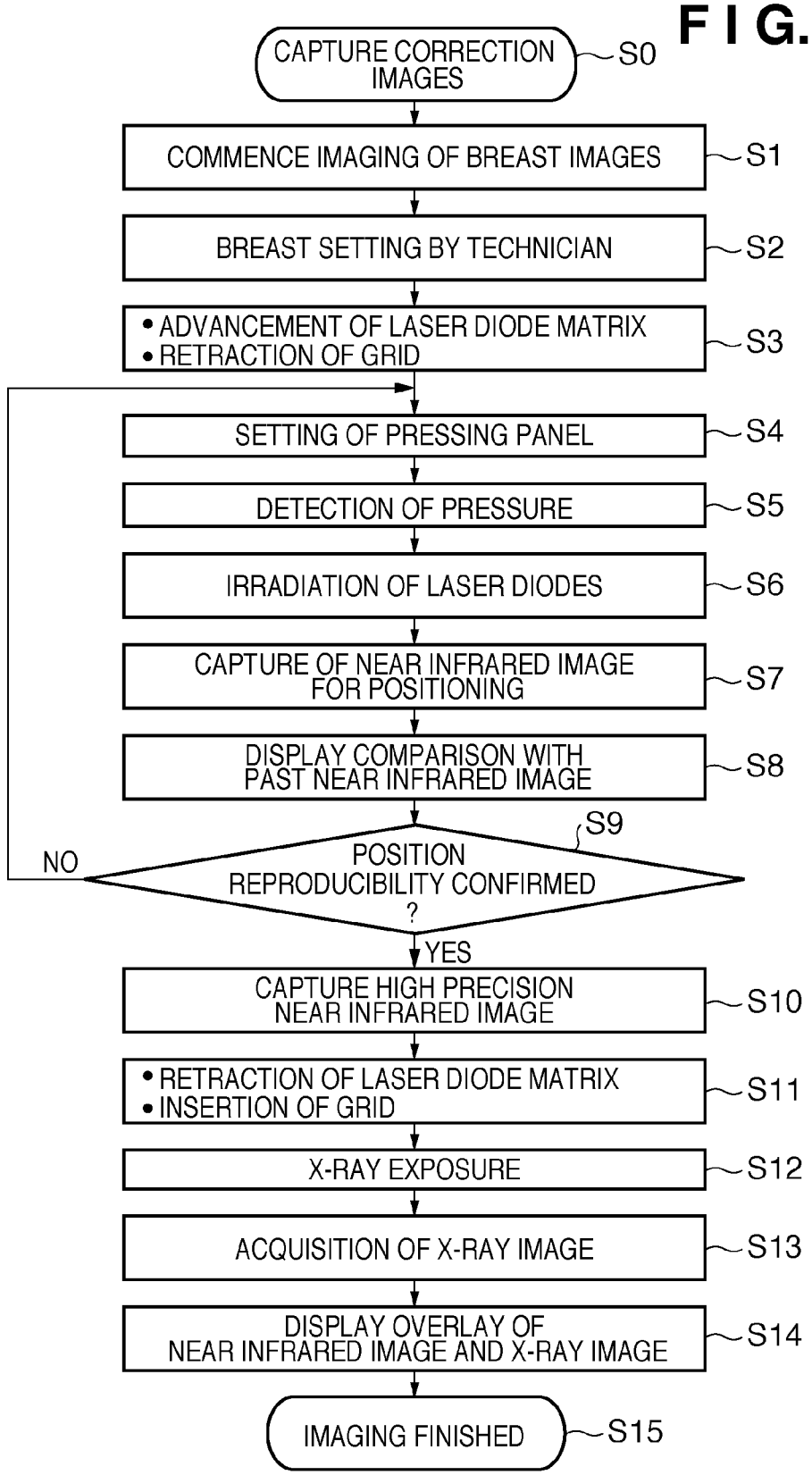
FIG. 8 is a flowchart of a control process relating to X-ray breast imaging according to the present embodiment.

Finally, description is given using a flowchart of FIG. 8 of a control process relating to X-ray breast imaging according to the present embodiment.

Acquisition of a correction image is carried out at S0 before imaging of a patient. Correction images are acquired immediately prior to patient imaging giving consideration to temperature drift of the two-dimensional detector 5.

Imaging of the patient commences at S1. At S2, the technician performs initial setting of the breast 6 of the patient on an imaging platform. At S3, the laser diode matrix 2 advances to a first position in close contact with the pressing panel 3, and the X-ray grid 4 retracts. At S4, the pressing panel 3 is lowered by operation of the technician, and when pressure is detected at S5, light is emitted from the laser diodes at S6 and imaging commences.

When exposure from each laser diode and transmitted light detection is completed at S7, a comparison is carried out with a past near infrared image at S8. The comparison may also involve displaying a difference image.

At S9, a confirmation of position reproducibility is carried out. If reproducibility is confirmed, a high precision near infrared image is captured at S10.

At S11, the laser diode matrix 2 retracts to a second position outside an X-ray image capture region, and the X-ray grid 4 is inserted. At S12, X-ray exposure is carried out and at S13, X-ray image acquisition is carried out. The near infrared image and the X-ray image are captured under identical conditions, and therefore at S14 it is possible to carry out image processing overlaying the images without needing to perform geometrical conversions. The X-ray image displayed in black and white and the near infrared image displayed in color can be overlaid. At S15, imaging is completed.

With the present invention, reproduction of breast settings (capture method) is possible in X-ray breast imaging.

This enables near infrared images and X-ray images to be captured under identical conditions.

Furthermore, by displaying an overlay of the near infrared image and the X-ray image, an overlay of calcified cancer and tumorous cancer can be carried out with excellent accuracy.

Furthermore, it becomes possible to estimate an appropriate imaging dose when transitioning from a near infrared image to X-ray imaging.

Further still, images having excellent contrast can be achieved by capturing in advance images for correction of the near infrared image and the X-ray image respectively from the same sensor.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

An embodiment of the present invention can provide a mammography apparatus for capturing an X-ray image of a breast, comprising: an X-ray source; a detector having a placement surface on which a breast is placed on a side opposing the X-ray source and that detects X-rays transmitted through the breast, wherein the detector is capable of detecting near infrared rays as well as being capable of detecting X-rays; an optically transparent or semitransparent pressing panel for pressing the breast that is placed on the placement surface against the placement surface; a two-dimensional near infrared ray source that is provided between the X-ray source and the pressing panel and arranged in a two-dimensional shape in alignment with the pressing panel, and that is movable between a first position in close contact with the pressing panel and a second position outside an X-ray image capture region, and a controller that carries out near infrared image capture using the two-dimensional near infrared ray source by causing the two-dimensional near infrared ray source to be in the first position, and causes the two-dimensional near infrared ray source to retract to the second position when carrying out X-ray image capture using the X-ray source.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A detecting apparatus comprising:
   a wavelength filter configured to transmit at least near-infrared rays and not to transmit visible light;
   a phosphor configured to transmit near-infrared rays transmitted through the wavelength filter, and to generate fluorescence with respect to incident X-rays;
   a semiconductor sensor configured to sense near-infrared rays transmitted through the phosphor and the fluorescence; and
   a controller configured to control to read clusters of a predetermined number of pixels of the semiconductor sensor when the near-infrared rays are generated from a near-infrared ray source, so as to readout images at high speed in relation to an X-ray imaging.

2. The detecting system according to claim 1, wherein the detecting system is incorporated in an imaging system that includes an image processor configured to overlay a near-infrared image, which is captured using the detecting system, and an X-ray image.

3. The apparatus according to claim 1, wherein the phosphor is provided between the wavelength filter and the semiconductor sensor.

4. The apparatus according to claim 1, further comprising a protective panel provided on a side of an incident surface of the wavelength filter, and having a placement surface on which an object is placed.

5. The apparatus according to claim 4, further comprising an optically transparent or semitransparent pressing panel for pressing an object that is placed on the placement surface against the placement surface.

6. The apparatus according to claim 5, wherein the controller controls so that the near-infrared rays are irradiated from a near-infrared ray source when pressure on the pressing panel is detected.

7. The apparatus according to claim 5, further comprising a grid provided between the pressing panel and the wavelength filter.

8. The apparatus according to claim 7, wherein when the near-infrared rays are irradiated from a near-infrared ray source, the controller controls the grid to evacuate from an irradiation area of the near-infrared rays.

9. The apparatus according to claim 1, wherein when carrying out capture of a near-infrared image for positioning of an object, the controller carries out decimated lighting of the near-infrared ray source.

10. The apparatus according to claim 1, wherein when carrying out capture of a near-infrared image for positioning of an object, the controller controls a display to display a difference image between the captured near-infrared image and a previously captured near-infrared image.

11. The apparatus according to claim 1, wherein when carrying out capture of a near-infrared image for positioning of an object, the controller controls a display to display the captured near-infrared image in parallel to a previously captured near-infrared image.

12. The apparatus according to claim 1, further comprising an image processor configured to overlay a captured near-infrared image and an X-ray image.

13. The apparatus according to claim 1, wherein the phosphor comprises a columnar crystal.

14. The apparatus according to claim 13, wherein the columnar crystal comprises a CsI.

15. The apparatus according to claim 1, wherein the semiconductor sensor comprises a CMOS sensor.

16. The apparatus according to claim 1, wherein
   the semiconductor sensor has sensitivity to near-infrared rays having a plurality of wavelength, and
   the apparatus further comprising a processor configured to process signals output from the apparatus as X-ray images when an X-ray is irradiated, and process the signal as near-infrared images each corresponding to the plurality of wavelength when an X-ray does not irradiated and the near-infrared rays having the plurality of wavelength are irradiated.

17. The apparatus according to claim 16, wherein
   each of the near-infrared rays having each of the plurality of wavelength undergoes amplitude modulation at a different predetermined frequency,
   the apparatus further comprising an amplifier configured to amplify an output signal of the semiconductor sensor with a gain which is changed by a gain change signal of the predetermined frequency,
   the processor separates the gain change signal to obtain images each corresponding to the respective wave length.

18. The apparatus according to claim 17, wherein the semiconductor sensor comprises a plurality of pixels arranged two-dimensionally, and the amplifier amplifies an output signal of each of the plurality of pixels.

19. The apparatus according to claim 1, wherein a near-infrared ray source of the near-infrared rays generates near-infrared rays having a plurality of wavelength.

20. The apparatus according to claim 16, further comprising an image processing unit configured to obtain a spectoroscopy by combining a plurality of images obtained by the processor.

* * * * *